(12) United States Patent
Guillemot et al.

(10) Patent No.: US 9,629,989 B2
(45) Date of Patent: Apr. 25, 2017

(54) BIOPRINTING STATION, ASSEMBLY COMPRISING SUCH BIOPRINTING STATION AND BIOPRINTING METHOD

(71) Applicants: Fabien Guillemot, Bordeaux (FR); Sylvain Catros, Bordeaux (FR); Virginie Keriquel, Bordeaux (FR); Jean-Christophe Fricain, Bordeaux (FR)

(72) Inventors: Fabien Guillemot, Bordeaux (FR); Sylvain Catros, Bordeaux (FR); Virginie Keriquel, Bordeaux (FR); Jean-Christophe Fricain, Bordeaux (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 14/692,821

(22) Filed: Apr. 22, 2015

(65) Prior Publication Data
US 2015/0224291 A1    Aug. 13, 2015

Related U.S. Application Data

(62) Division of application No. 13/582,145, filed as application No. PCT/EP2011/005331 on Mar. 4, 2011, now Pat. No. 9,039,998.

(30) Foreign Application Priority Data

Mar. 4, 2010    (EP) .................................... 10305224

(51) Int. Cl.
*B01L 3/02* (2006.01)
*A61M 35/00* (2006.01)
(Continued)

(52) U.S. Cl.
CPC ........... *A61M 35/00* (2013.01); *B01L 3/0268* (2013.01); *C12M 1/26* (2013.01); *C12M 21/08* (2013.01);
(Continued)

(58) Field of Classification Search
CPC ................................ B01L 3/02; B01L 3/0237
See application file for complete search history.

(56) References Cited

U.S. PATENT DOCUMENTS 6,177,151 B1   1/2001   Chrisey et al.
6,864,101 B1   3/2005   Winkler et al.
(Continued)

FOREIGN PATENT DOCUMENTS

WO         03056320 A2    7/2003
WO      2005107949 A1   11/2005

OTHER PUBLICATIONS

Ringeisen et al., "Generation of mesoscopic patterns of viable *Escherichia coli* by ambient laser transfer", Biomaterials, Jan. 1, 2002, vol. 23, pp. 161-166, Elsevier.

*Primary Examiner* — Jan Ludlow
(74) *Attorney, Agent, or Firm* — Whitham, Curtis & Cook, P.C.

(57) ABSTRACT

Bioprinting station (1) comprising:—a Bioprinting device (4) adapted to deposit a pattern of biological material (2) onto an area of interest (3a) of a substrate (3),—an imaging system (15) adapted to acquire an image of the substrate (3) and to reveal on the acquired image the area of interest (3a) with respect to a remaining part (3b) of the substrate (3), the acquired image of the substrate (3) being processed so as to detect the revealed area of interest (3a) on the acquired image and to determine the pattern corresponding to the area of interest (3a) detected on the acquired image.

5 Claims, 8 Drawing Sheets

(51) Int. Cl.
  *C12M 1/26* (2006.01)
  *C12M 3/00* (2006.01)
  *B33Y 80/00* (2015.01)
  *B01L 3/00* (2006.01)
  *G01N 35/10* (2006.01)

(52) U.S. Cl.
  CPC ............ *C12M 33/00* (2013.01); *C12M 33/04* (2013.01); *B01L 3/502761* (2013.01); *B01L 2200/0647* (2013.01); *B01L 2200/143* (2013.01); *B01L 2400/0454* (2013.01); *B33Y 80/00* (2014.12); *G01N 2035/1041* (2013.01)

(56) References Cited

U.S. PATENT DOCUMENTS

| | | |
|---|---|---|
| 2003/0157271 A1 | 8/2003 | Duignan et al. |
| 2004/0022689 A1 | 2/2004 | Wulf et al. |
| 2008/0038487 A1 | 2/2008 | Barron et al. |
| 2011/0172611 A1 | 7/2011 | Yoo |

BIOPRINTING STATION, ASSEMBLY COMPRISING SUCH BIOPRINTING STATION AND BIOPRINTING METHOD

CROSS-REFERENCE TO RELATED APPLICATIONS

This application is a divisional application of U.S. Ser. No. 13/582,145 filed Sep. 17, 2012, now U.S. Pat. No. 9,039,998, which itself was a Rule 371 national stage filing of PCT/EP2011/005331 filed Mar. 4, 2011, which claimed priority to European Application 10305224.7 filed Mar. 4, 2010.

The invention relates to a Bioprinting station, to an assembly comprising such Bioprinting station and to a Bioprinting method.

In particular, the invention relates to Bioprinting (biological printing) station comprising:

a Bioprinting device adapted to deposit a pattern of biological material (including cells, cell aggregates, biomaterials, nanoparticles, drugs and other molecules having a biological effect on cells of a tissue, and others), onto an area of interest of a substrate, said area of interest having a feature (recess, specific morphology, optical feature, marking or other) that distinguishes said area of interest from a remaining part of the substrate, said Bioprinting device comprising:

at least one biological material dispenser adapted to dispense the biological material to be deposited, and a positioning system adapted to receive the substrate and to position the area of interest with respect to the dispenser, an electronic control unit adapted to drive the dispenser and the positioning system relative to one another according to the pattern to be deposited.

Although not limited thereto, the invention has particularly advantageous applications in the treatment of loss of tissue architecture (including multiple cell types and matrix components precisely organized in three dimensions) caused for example by a trauma or a disease and which leads to loss of tissue function.

It has been found that such loss of tissue architecture could be treated through generation of biological tissues involving the use of engineering and material methods to obtain the appropriate combination of cells and the suitable biochemical and physicochemical factors which mimic both the micro-environment of cells and the micro-architecture of tissue in the body. In this context, tissue engineering which aims to provide for biological substitutes which restore, maintain or improve tissue function or a whole organ has been developed.

At first, living cells have been seeded onto biocompatible, and eventually biodegradable, scaffold and cultured in a bioreactor to lead to an initial cell population expanding into a tissue. With an appropriate scaffold which mimics the biological extracellular matrix, the developing tissue can adopt both the form and the function of the desired organ, and can be implanted into the body of patient.

In parallel with the aforementioned method, the building of three-dimensional (3D) biological structures by the technology of Bioprinting has been considered ("Application of laser printing to mammalian cells", J. A. Barron, B. R. Ringeisen, H. Kim, B. J. Spargo, et D. B. Chrisey, *Thin Solid Films*, vol. 453-454, April 2004, 383-387; "Quantification of the activity of biomolecules in microarrays obtained by direct laser transfer", V. Dinca, A. Ranella, M. Farsari, D. Kafetzopoulos, M. Dinescu, A. Popescu, et C. Fotakis, *Biomedical Microdevices*, vol. 10, October 2008, 719-25).

Bioprinting consists in an automated, computer-aided layer-by-layer deposition, transfer and patterning of biological materials including cells and cell aggregates ("Organ printing: computer-aided jet-based 3D tissue engineering", V. Mironov, T. Boland, T. Trusk, G. Forgacs, and R. R. Markwald, *Trends in Biotechnology*, vol. 21, April 2003, 157-161; "Biofabrication: a 21' century manufacturing paradigm", V. Mironov, T. Trusk, V. Kasyanov, S. Little, R. Swaja, et R. Markwald, *Bio fabrication*, vol. 1, 2009, p. 022001; "Jet-based methods to print living cells", B. R. Ringeisen, C. M. Othon, J. A. Barron, D. Young, et B. J. Spargo, *Biotechnology Journal*, vol. 1, September 2006, 930-48). Recently, the definition of bioprinting was enlarged to "the use of computer-aided transfer processes for patterning and assembling living and non-living materials with a prescribed 2D or 3D organization in order to produce bio-engineered structures serving in regenerative medicine, pharmacokinetic and basic cell biology studies" (F. Guillemot, V. Mironov, M. Nakamura, *Bio fabrication*, vol. 2, 2010).

To this end, commercially available inkjet printers have been redesigned ("Application of inkjet printing to tissue engineering", T. Boland, T. Xu, B. Damon, and X. Cui, *Biotechnology Journal*, vol. 1, 2006, 910-917) or new ones built ("Biocompatible inkjet printing technique for designed seeding of individual living cells", Makoto Nakamura, Akiko Kobayashi, Fumio Takagi, Akihiko Watanabe, Yuko Hiruma, Katsuhiro Ohuchi, Yasuhiko Iwasaki, Mikio Horie, Ikuo Morita, Setsuo Takatani, *Tissue Eng* 2006; "Delivery of human fibroblast cells by piezoelectric drop-on-demand inkjet printing", Saunders R E, Gough J E, Derby B., *Biomaterials* 2008; 29: 193-203.) to pattern biological assemblies according to a computer-aided design template. Pressure-operated mechanical extruders such as bioplotters have also been developed to handle live cells and cell aggregates ("Tissue Engineering by Self-Assembly of Cells Printed into Topologically Defined Structures", K. Jakab, C. Norotte, B. Damon, F. Marga, A. Neagu, C. L. Besch-Williford, A. Kachurin, K. H. Church, H. Park, V. Mironov, R. Markwald, G. Vunjak-Novakovic, and G. Forgacs, *Tissue Engineering Part A*, vol. 14, 2008, 413-421).

Parallel to these Bioprinting methods, laser-assisted printing has emerged as an alternative method for the assembly and micro-patterning of biological materials.

Laser-guided direct writing (LGDW) is a technique capable of trapping multiple cells in a laser beam and depositing them as a steady stream onto arbitrary non-absorbing surfaces ("Laser-guided direct writing for three-dimensional tissue engineering" Nahmias Y, Schwartz R E, Verfaillie C M, Odde D J, *Biotechnol Bioeng* 2005; 92: 129-36; "Micropatterning of living cells by laser-guided direct writing: application to fabrication of hepatic-endothelial sinusoid-like structures", Yaakov Nahmias, David J. Odde, *Nat Protoc* 2006).

Laser-Assisted Bioprinting (LAB) is based on the laser-induced forward-transfer (LIFT) technique in which a pulsed laser is used to induce the transfer of biological material from a ribbon as a reservoir, formed of a layer of biological material spread onto an optically transparent quartz support, to a substrate in close proximity to or in contact with the ribbon ("Laser printing of pluripotent embryonal carcinoma cells", Ringeisen B R, Kim H, Barron J A, Krizman D B, Chrisey D B, Jackman S, Auyeung R Y C, Spargo B J, *Tissue Eng* 2004; 10: 483-91).

Known Laser-Assisted Bioprinting methods comprise matrix assisted pulsed laser evaporation-direct write (MAPLE-DW) ("Application of laser printing to mammalian cells", Barron J A, Ringeisen B R, Kim H, Spargo B J, Chrisey D B, *Thin Solid Films* 2004: 383-7), absorbing film assisted-LIFT (AFA-LIFT) ("Survival and proliferative ability of various living cell types after laser-induced forward transfer", Bela Hopp, Tomi Smausz, Norbert Kresz, Norbert Barna, Zsolt Bor, Lajos Kolozsvari, Douglas B. Chrisey, Andras Szabo, Antal Nogradi, *Tissue Eng* 2006) and Laser-Assisted Bioprinting (LAB) ("Laser-Assisted Bioprinting: a novel technique for creating heterogeneous 3-dimensional cell patterns", Barron J A, Wu P, Ladouceur H D, Ringeisen B R, *Biomed Microdev* 2004; 6: 139-47; "Laser printing of single cells: statistical analysis, cell viability, and stress", Barron J A, Krizman D B, Ringeisen B R, Ann Biomed Eng 2005; 33: 121-30). Using LAB, under suitable irradiation conditions, and for liquids presenting a wide range of rheologies, the material can be deposited in the form of well-defined circular droplets with a high degree of spatial resolution.

The invention aims to improve the accuracy in the determination of the pattern of the Bioprinting in order to deposit a pattern of biological material that accurately matches the area of interest onto which this pattern of biological material has to be deposited.

To this end, the invention proposes a Bioprinting station of the aforementioned type comprising an imaging system adapted to acquire an image of the substrate and to reveal on the acquired image the feature of the area of interest with respect to the remaining part, the acquired image of the substrate being processed so as to detect the revealed area of interest on the acquired image and to determine the pattern corresponding to the area of interest detected on the acquired image.

Hence, the Bioprinting station according to the invention provides for an automated direct acquisition of the area of interest onto which the pattern is to be deposited and to determine the pattern specific to the area of interest shown on the acquired image. The deposited pattern of biological material can therefore accurately match the area of interest, shown for example by contrast with respect to the remaining part of the substrate on the acquired image of the substrate and detected by an operator through the control unit or automatically by the control unit, and the overall accuracy of the Bioprinting can be improved.

In an embodiment, the electronic control unit is adapted to process the acquired image of the substrate so as to automatically detect the revealed area of interest on the acquired image and to automatically determine the pattern corresponding to the area of interest detected on the acquired image.

The electronic control unit may further be adapted to determine a location of the area of interest in a reference frame of the Bioprinting station and to drive the dispenser and the positioning system relative to one another according to the determined location. An automated location of the area of interest can, therefore, be provided.

Besides, to improve accuracy, the electronic control unit may be adapted to drive the imaging system according to an optical pathway corresponding to the determined pattern to be deposited. In doing so, the imaging system can follow the dispensing of the biological material.

In a particular advantageous embodiment, the Bioprinting station implements Laser-Assisted Bioprinting.

In this respect, the dispenser may comprise:

a holding device for holding at least one ribbon containing the biological material, the holding device being provided with at least one opened working space adapted to receive at least a part of the ribbon, the electronic control unit being adapted to drive the holding device and the positioning system relative to one another so that the opened working space faces the area of interest, a laser system arranged for emitting a laser beam adapted to transfer the biological material from the ribbon to the substrate, the electronic control unit being adapted to drive the laser system so as to direct the laser beam according to the determined pattern within the opened working space.

In particular, the laser system may comprise a laser device for emitting the laser beam, such as an infra-red pulsed laser, and an optical scanning device adapted to orient the laser beam within the opened working space.

A ribbon, acting as a reservoir for the biological material, may then be received at least partly in the opened working space of the holding device, the ribbon presenting a first surface that faces the laser system and a second surface provided with a layer of biological material, said second surface facing the positioning system. The ribbon may comprise a support transparent to the laser beam and coated with the layer of biological material, and an intermediate transduction layer arranged between the support and the layer of biological material.

Such Laser-Assisted Bioprinting station is in line with the development of computer-assisted medical interventions (CAMI) resulting from converging evolutions in medicine, physics, materials, electronics, informatics, robotics, etc. CAMI aims at providing tools that allow the clinician to use multimodality data in a rational and quantitative way in order to plan, to simulate and to execute mini-invasive medical interventions accurately and safely. Medical interventions include both diagnostic and therapeutic actions (surgery, radiotherapy, local injection of drugs, etc.). In this aim informatics and micro-technology have accompanied the evolution of the clinical practice and paved the way for robotic applications at the bedside. Indeed, thanks to CAMI:

(i) more and more data are handled for each patient (e.g. images, signals) during preparation and/or monitoring medical actions, (ii) traceability and quality control have been organized, and (iii) diagnostic and therapy procedures tend to be less and less invasive.

Moreover, medical robotics have been improved by the development of automation, what provides assistance to the clinician where his abilities (or presence) are limited. In medicine, like in many fields, the robot advantages come from precision, ability to repeat a task endlessly, potential connection to computerized data and sensors, or other capability to operate in hostile environments. From an operating point of view, potential specific robot abilities are for instance:

(i) to realize complex geometric tasks (e.g. to machine a 3D bone cavity), (ii) to be force-controllable down to very small force scales, (iii) to execute high resolution, high accuracy motions (for microsurgery), (iv) to track moving organs and to be synchronized to external events based on some signals, and else (v) to be introduced in the patient for intra-body actions.

Actually, the Laser-Assisted Bioprinting station can be a part of a medical assembly adapted to perform different tasks with respect to therapy and surgical treatments. In particular, the laser device itself can be used for other tasks than transferring the biological material from the ribbon to the substrate, such as ablation, machining, heating, welding, etc.

When implemented in tissue engineering, the Bioprinting device may be adapted to form a biological tissue structure through deposition of the pattern of biological material, the area of interest having a relief with respect to the remaining part of the substrate as feature, said relief having a geometry, the imaging system being adapted to reveal on the acquired image the relief, the revealed relief being detected on the acquired image and the pattern corresponding to the geometry of the relief detected on the acquired image being determined, so as to form the biological tissue structure corresponding to the relief.

The electronic control unit may be adapted to automatically detect the revealed relief on the acquired image and to automatically determine the pattern corresponding to the geometry of the relief detected on the acquired image.

The invention has been found to be of particular interest in the application of forming a biological tissue structure, in 2D or 3D through a layer-by-layer deposition of biological material (including cells and cell aggregates in such application), onto a recess of the substrate as area of interest. In such application, the imaging system is adapted to measure a difference in the distance between the substrate and the biological material dispenser, and to show this difference trough a corresponding contrast on the image of the substrate. The invention is, however, not limited to such application and can be implemented in other application, such as the treatment of other disease and trauma. For example, the Bioprinting station could be implemented for the deposition of drugs or other molecules having a biological effect on cells of a tissue as biological material onto determined cells, such as cells of a tumor, that can be shown by contrast with the remaining part of the substrate. In this respect, the cells may have a specific arrangement detectable by the imaging system or can be marked by a suitable marker previously attached thereto, so as to present an optical feature that can be revealed by an appropriate setting of the imaging system (filter, . . . ).

According to another aspect, the invention proposes an assembly comprising a Bioprinting station as defined above, and a substrate presenting at least one area of interest and a remaining part, said area of interest having the feature that distinguishes said area of interest from the remaining part, the substrate being arranged in the positioning system.

When implemented in tissue engineering, the area of interest may have a relief, such as a recess, with respect to the remaining part of the substrate, said relief having a geometry, the Bioprinting station being adapted to form the biological tissue structure corresponding to the relief.

According to a further aspect, the invention proposes a Bioprinting method comprising the following steps:

A—providing a Bioprinting device adapted to deposit a pattern of biological material, B—providing a substrate presenting at least one area of interest and a remaining part, said area of interest having a feature that distinguishes said area of interest from the remaining part, C—positioning the area of interest with respect to the Bioprinting device D—acquiring an image of the substrate and revealing on the acquired image the feature of the area of interest, E—processing the acquired image of the substrate so as to detect the revealed area of interest on the acquired image and to determine the pattern corresponding to the area of interest detected on the acquired image, F—depositing the biological material according to the determined pattern onto the area of interest.

In an embodiment, the step E may comprise automatically detecting the revealed area of interest on the acquired image and automatically determining the pattern corresponding to the area of interest detected on the acquired image.

In a particular embodiment, the area of interest of the substrate has a relief with respect to the remaining part of the substrate as feature, said relief having a geometry, and the step D comprises revealing on the acquired image the relief, the step E comprises detecting the revealed relief on the acquired image and determining the pattern corresponding to the geometry of the relief detected on the acquired image, and the step F comprises forming a biological tissue structure corresponding to the relief.

Besides, the step E may further comprise determining a location of the area of interest, and the step F may comprise depositing the biological material at the determined location.

Other objects and advantages of the invention will emerge from the following disclosure made in reference to the enclosed drawings in which.

On the Figures, the same references refer to same or analogous elements.

Figure 1:
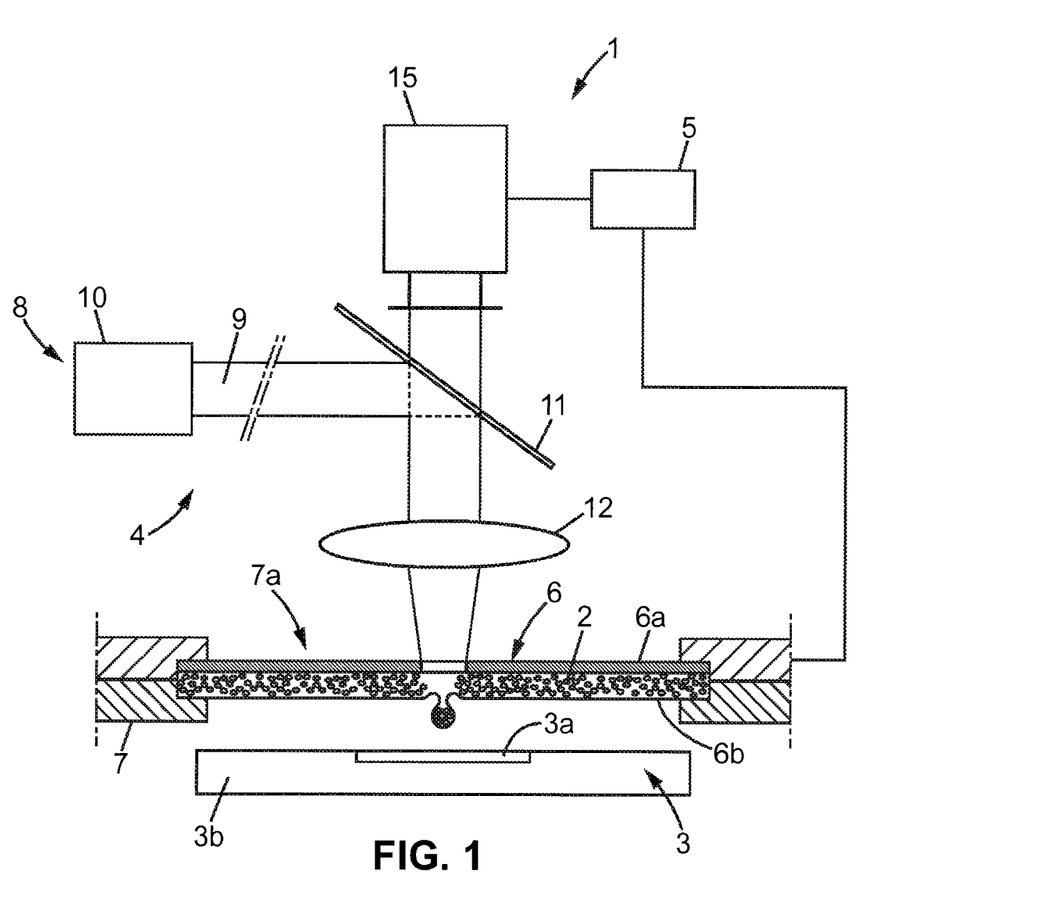
FIG. 1 is a schematic view of a Bioprinting station according to an embodiment of the invention, the Bioprinting station being adapted for Laser-Assisted Bioprinting of a biological tissue structure.
Figure 2:
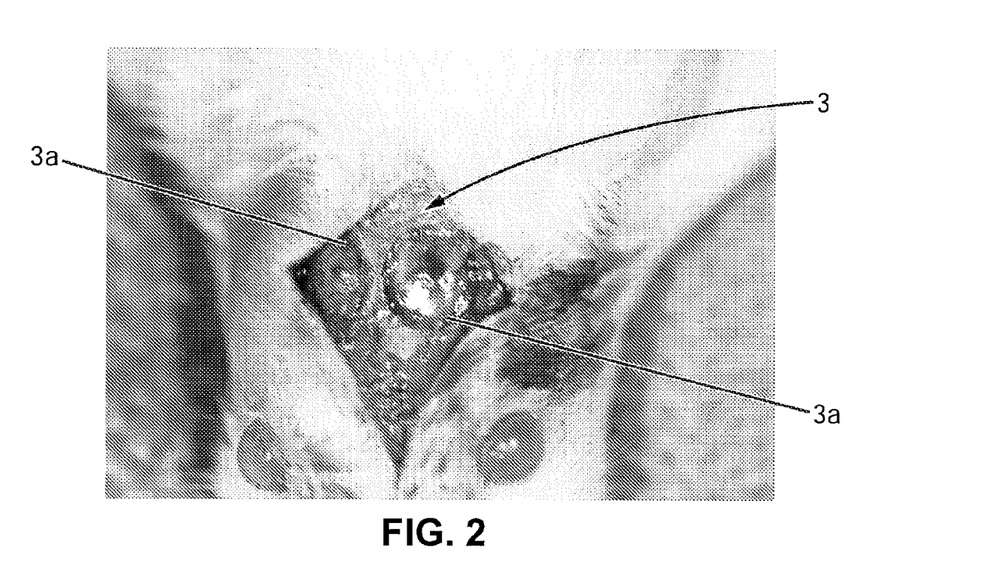
FIG. 2 is a view of two calvaria defects performed on a mouse in a first experimentation implementing the Bioprinting station of FIG. 1, the first experimentation consisting in an in vivo treatment of one of the two mouse calvaria defects, as test site, by printing biological material (nano-hydroxyapatite, n-HA) suitable to promote growth of bone tissue within the mouse calvaria defects at the test site, the other mouse calvaria defect being left empty as a control site.

FIG. 1 schematically represents a Bioprinting station 1 adapted to deposit on a substrate 3 biological material 2 for a therapeutic or surgical treatment of a tissue of a body.

In this respect, the biological material 3 can be any suitable biological material having therapeutic or surgical effect, including living cells and cell aggregates, as well as drugs or any molecule adapted to interact with the cells of the tissue.

The substrate 3 forms a support onto which the biological material can be received in order to interact with cells of the tissue, to be cultured or to grow. In particular, the biological material 2 can be printed directly on a substrate 3 formed by a part of the body itself, or indirectly, the deposited biological material 2 being subsequently implanted, together with the substrate 3 or not. In the later case, the substrate 3 can be a cell culture, a natural tissue extracted from the body, an artificial tissue or a scaffold, especially made of biocompatible or implantable material, or other.

The invention is disclosed, in particular, in relation to a Bioprinting station 1 dedicated to High-Throughput Laser-assisted Bioprinting (HT-LAB) for an application in tissue engineering, given as an illustrative non-limiting example. Such station permits to print different types of biological material 2 at micrometer resolution, especially for the assembly of complex two-dimension (2D) or three-dimension (3D) biological tissue structures.

In particular, the described Laser-Assisted Bioprinting station 1 can be used to form a biological tissue structure intended to restore, maintain or improve a tissue having a defect through the deposition of a pattern accurately corresponding to shape of the defect.

As can be seen on FIG. 1, the substrate 3, made either directly of the tissue to be repaired or of any other appropriate support which allows for a subsequent effect or interaction with the cells of the tissue, presents at least one area of interest 3a onto which the biological material 2 has to be printed, and a remaining part 3b.

The area of interest 3a has a feature that distinguishes this area of interest 3a from the remaining part 3b. In the illustrated example, the area of interest 3a is a recess that distinguishes from the remaining part 3b of the substrate 3 trough an upper surface internally offset with respect to that of the remaining part 3b. The area of interest 3a could, however, be any other kind of relief providing for a level difference of surface with respect to the remaining part 3b.

The deposition of biological material 2 can be performed directly onto the area of interest 3a forming the defect of the tissue itself, or indirectly apart from the tissue, onto an area of interest having a geometry which matches that of the defect, the resulting biological tissue structure being then implanted in the defect of the tissue.

It should be noted that the invention could be implemented in any other kind of laser assisted bioprinting station, using for example LGDW, MAPLE-DW or AFA-LIFT. More generally, the invention could be used in any other kind of Bioprinting station, including inkjet printers, pressure-operated mechanical extruders such as bioplotters, micro-contact printing, lithography and others.

Moreover, the invention is not limited to an application in tissue engineering and could be implemented for the treatment of other disease and trauma. Actually, the Bioprinting station can be used for accurately depositing drugs or other active substance onto cells identified in an appropriate manner, for example though the use of a marker providing to the cells a feature, such as an optical feature, different from that of the remaining part of the substrate.

The Bioprinting station 1 comprises a Bioprinting device 4 adapted to deposit the pattern of biological material 2 and controlled by an electronic control unit 5.

The Bioprinting device 4 comprises at least one biological material dispenser and a positioning system, not shown, which receives the substrate 3. The dispenser and the positioning system are arranged relative to one another so as to permit deposition of the biological material 2 onto the substrate 3. The control unit 5, electronic, is connected to the dispenser and to the positioning system so as to move at least one of them, for example the positioning system, with respect to the other in order to position the area of interest 3a with respect to the dispenser.

An example of a suitable Laser-Assisted Bioprinting Laser-assisted Bioprinting device 4 is disclosed in the articles "High-throughput Laser Printing of Cells and Biomaterials for Tissue Engineering", F. Guillemot, A. Souquet, S. Catros, B. Guillotin, J. Lopez, M. Faucon, B. Pippenger, R. Bareille, M. Remy, S. Bellance, P. Chabassier, J. Fricain, et J. Amédée, *Acta Biomaterialia*, 2009 and "Self-consistent modeling of jet formation process in the nanosecond laser pulse regime", C. Mézel, L. Hallo, A. Souquet, J. Breil, D. Hebert, and F. Guillemot. Phys. Plasmas 16, 123112 (2009).

The positioning system is for example made of a sophisticated five-axe positioning system with the purpose of printing multi-color patterns and building 3D biological structures. The substrate 3 can be held with a (x, y, z) motorized micrometric translation stage whose resolution is 1 μm for longitudinal x and transverse y axes and 5 μm for vertical axis z.

Besides, in this Laser-Assisted Bioprinting device 4 schematically illustrated on FIG. 1, the dispenser comprises:
  a ribbon 6 forming a reservoir of biological material 2, the ribbon 6 having a first surface 6a and a second surface 6b opposite to the first surface 6a and provided with a layer of biological material 2, the second surface 6b facing the positioning system and the substrate 3, a holding device 7 provided with an opened working space 7a into which a central part of the ribbon 6 extends, opposite edges of the ribbon 6 on either sides of the central part being removably held by the holding device 7, a laser system 8 arranged for emitting a laser beam 9 adapted to transfer the biological material 2 from the ribbon 6 to the substrate 3, the laser system facing the first surface 6a of the central part of the ribbon 6.

As can be seen on FIG. 1, the ribbon 6 comprises a support transparent to the laser beam, for example a disk made of IR-transparent quartz, and coated with the layer of biological material 2. In the example, the Laser-Assisted Bioprinting device 4 performs an absorbing film assisted-LIFT (AFA-LIFT). An intermediate transduction layer is therefore arranged between the support and the layer of biological material 2 to change the optical energy receive by the laser beam 9 into mechanical energy to transfer the biological material 2. The ribbon 6 could, however, be adapted to any other kind on laser printing method, where such intermediate transduction layer is not used.

In order to achieve multi-color printing, the holding device 7 may consists in a high resolution (1° angular resolution) motorized carousel rotatably mounted with respect to the laser system 8 and provided with several opened working space receiving respective ribbons 6 provided with different biological materials 2. In particular, the carousel may have a loading capacity of five different ribbons 6. The substrate positioning system and carousel are held on the same vertical axis with the aim of varying focusing conditions without changing the gap distance. The holding device is connected to the control unit 5 so that each opened working space may face the area of interest 3a of the substrate 3.

The laser system 8 comprises a laser device 10 for emitting the laser beam 9 and an optical scanning device adapted to orient the laser beam 9 within the opened working space 7a and onto the first surface 6a of the ribbon 6.

For example, the laser device 10 may be an infra-red pulsed laser having a wavelength $\lambda$ which avoids inducing alteration of the biological materials used. In particular, a solid Nd:YAG crystal laser (Navigator I, Newport Spectra Physics) may be selected with the following specifications: $\lambda=1064$ nm, s=30 ns, f=1-100 kHz, q=3.4 mrad, TEM00, ptp<1.5% rms, P=7 W. In other embodiments, however, a UV laser could be used.

Besides, deposition of biological material 2 through droplet generation from the second surface 6b of the ribbon 6 can be performed by driving the laser beam 9 by means of the optical scanning device comprising, for example, a high speed scanning system composed of two galvanometric mirrors 11 (SCANgine 14, ScanLab), with a scanning speed reaching 2000 mm·s$^{-1}$, and a large field optical F-theta lens 12 (S4LFT, Sill Optics, France) (F=58 mm).

The laser system is connected to the control unit which controls the laser parameter of the laser device 10 and drives the galvanometric mirrors 11 and the optical F-theta lens 12 so as to direct the laser beam 9, having the suitable parameters to cause transfer of the biological material, according to a determined pattern onto the first surface 6a of the ribbon 6.

As can be seen on FIG. 1, the Bioprinting station further comprises an imaging system 15, such as a CCD camera and/or any other suitable imaging device adapted to provide anatomical and/or functional images, for example a photon imager, MRI, fMRI, PET or other, connected to the control unit 5 and driven according to an optical pathway corresponding to the determined pattern to be deposited for focal setting in the ribbon 6 and (x, y, z) substrate positioning carried out through the optical scanning system 11, 12.

According to the invention, the imaging system 15 is adapted to acquire an image of the substrate 3, for example through a scan performed by moving the optical pathway along the substrate, and to reveal the recess 3a with respect to the remaining part 3b of the substrate 3. In particular, the imaging system is sensitive to the surface offset between the upper surface of the recess 3a and that of the remaining part 3b and can show, for example by contrast, the recess 3a on the image of the substrate.

In applications where an area of interest other than a relief is to be detected, the imaging system 15 can be adapted accordingly to reveal the area of interest. For example, the area of interest can consist of cells of a different type from that of the remaining part, the imaging system 15 being adapted to detect the cells of the area of interest. In particular, the cells may have a spatial arrangement that makes them distinguishable from other cells. The cells of the area of interest can be illuminated or otherwise marked so as to be revealed by the imaging system 15 provided, where needed, with a suitable filter and/or suitable settings.

The control unit 5 includes instructions allowing the image of the substrate acquired by the imaging system 15 to be automatically processed so as to detect the revealed recess and to determine the pattern corresponding to the geometry of the recess 3a, so as to form the biological tissue structure corresponding to the recess 3a. Advantageously, a location of the recess 3a in a reference frame of the Bioprinting station can be made in an automated manner by the control unit processing the image of the substrate so as to drive the positioning system, the holding device 7 and/or the dispenser accordingly.

As an alternative, the image of the substrate acquired by the imaging system 15 can be processed by an operator. The operator may detect and possibly locate the revealed recess on the acquired image through the control unit 5, and may then determine and input the pattern that best fits the recess.

In relation to FIG. 1, the implementation of the above described Bioprinting station in a Bioprinting method is now disclosed. The Bioprinting method comprises the following steps:

placing the substrate 3 on the positioning system and placing the ribbon 6 on the holding device 7, driving the positioning system and the holding device 7 relative to each other to position the recess 3a of the substrate with respect to the opened working space 7a, driving the imaging device to scan the substrate 3 in order to obtain an image of the substrate, the imaging device being sensitive to surface offset so as to reveal the recess 3a, processing by the control unit, working in an automated manner or controlled by the operator, the image of the substrate so as to detect the revealed recess 3a and to determine both the location of the recess 3a and the pattern corresponding to the geometry of the recess 3a, moving the laser beam 9 onto the first surface 6a of the ribbon 6 according to the determined pattern to deposit, at the determined location, the biological material 2 according to the determined pattern onto the recess, so as to form a biological tissue structure corresponding to the geometry of the recess 3a.

In the illustrated example, the pulse duration z and the repetition rate f can be considered with the purpose of high throughput processes. Besides, the beam quality, including divergence q, spatial mode and pulse-to-pulse stability (ptp) must be taken into account to ensure the reproducibility, the stability and the high resolution of the system.

Actually, non-contact printing is obtained through jet formation which occurs ("Jet Formation in the laser forward transfer of liquids", M. Duocastella, J. Fernandez-Paras, P. Serra, et J. Morenza, *Applied Physics A: Materials Science and Processing*, vol. 93, 2008, 453-456), at a microsecond time scale, above a complex threshold whose value depends on the rheological properties and the thickness of liquid films, the thickness of the metallic absorbing layer as well as laser energy ("High-throughput Laser Printing of Cells and Biomaterials for Tissue Engineering", F. Guillemot, A. Souquet, S. Catros, B. Guillotin, J. Lopez, M. Faucon, B. Pippenger, R. Bareille, M. Rémy, S. Bellance, P. Chabassier, J. Fricain, et J. Amédée, *Acta Biomaterialia*, 2009; Self-consistent modeling of jet formation process in the nanosecond laser pulse regime", C. Mézel, L. Hallo, A. Souquet, J. Breil, D. Hébert, and F. Guillemot. *Phys. Plasmas* 16, 123112 (2009)).

By analogy with other studies in physics, it has been proposed that jet formation could be related to bubble dynamics. Bubble growth depends mainly on viscosity and surface tension of the liquid, while bubble collapsing is related to the distance between the bubble front and the free surface. Consequently, because droplet ejection is driven by bubble dynamics, high throughput LAB (HT-LAB) requires spatial-temporal proximity between two pulses and, thus two bubbles, to be taken into account in order to avoid the perturbation of the collapsing of the initial bubble by another.

The above described High-Throughput Laser-Assisted Bioprinting station can advantageously by used in tissue engineering to form a biological tissue structure, in two dimensions or three dimensions, intended to restore, maintain or improve a tissue having a defect through the deposition of a pattern accurately corresponding to the geometry of the defect. The deposition can be performed directly onto the defect and the tissue, or indirectly apart from the tissue and then implanted in the tissue.

For example, the above described High-Throughput Laser-Assisted Bioprinting station has been implemented in three particular experimentations detailed here below for tissue engineering to promote bone repair.

First Experimentation

The first experimentation described in relation to FIGS. 2 to 8 consists in depositing nano-hydroxyapatite (n-HA) into mouse calvaria defects of critical size, in vivo.

Materials and Methods

Synthesis of Printable n-HA

Nano-hydroxyapatite (n-HA) slurry was prepared via wet chemical precipitation at room temperature by dropping an orthophosphoric acid solution ($H_3PO_4$) into calcium hydroxide solution ($Ca(OH)_2$). TEM analysis of the dried synthesized material displayed 50 nm long needle-shaped crystals. FTIR analysis showed specific bands of phosphate ions at 559 $cm^{-1}$, 601 $cm^{-1}$ and 1018 $cm^{-1}$ and a non-specific carbonate band at 1415 $cm^{-1}$. X-Ray Diffraction (XRD) analysis of dried material revealed crystallites with hexagonal lattice parameters specific of hydroxyapatite.

For LAB experiments, 30% (v/v) glycerol was added to the n-HA solution at the end of the preparation. Sterilization of the n-HA containing suspension was performed by UV irradiation during 15 minutes. Biological properties of the powder material were previously tested in vitro and in vivo: it was shown that n-HA synthesized was biocompatible with osteoblastic cells and caused no inflammation in vivo in mice calvarial defects.

Ribbon Preparation

As described above, the ribbon is made of three layers: a support, a thin metal absorbing layer, as intermediate transduction layer, and a solution of hydrogel composed of a suspension of n-HA.

The support is a 30 mm diameter disk made of IR-transparent quartz. It was first coated with a thin absorbing layer of titanium (60 nm) using a high vacuum titanium coater. The thickness was chosen to be higher than the optical skin depth at near-IR wavelengths (1064 nm).

Then, 30 µl of the solution were spread on ribbon surface by the aid of a "doctor blade" device (Film Applicator 3570, Elcometer, France) to obtain a 30 µm thick layer of n-HA slurry.

Establishment of Calvaria Critical Size Defect in Mice

Thirty-six 12 week-old OF-1 male mice (Charles Rivers, France) were used for this study: Six were used to test infra red laser irradiation on mice brain and thirty were used for nHA in vivo printing They were first anesthetized with Ketamin and Xylazine through intraperitoneal injection. After skin antisepsis (Betadine), an incision was performed in skull midline and the scalp was dissected to expose the calvaria, then the periosteum was carefully peeled off. Two lateral 4 mm wide calvaria bone defects were performed (FIG. 2) in each animal with a 4 mm diameter trephine (TBR, Toulouse, France).

One defect was used for laser processing while the controlateral site was untreated as negative control.

The surgical procedures were performed under constant saline irrigation and care was taken to prevent dura mater injury. Then, the animals were placed inside the bioprinting station for in vivo printing experiments (see below). At the end of the experiment, the soft tissues were repositioned and sutured using 3/0 Vicryl. Animals recovered in a warm environment before being returned to animal facilities.

Effect of Near Infra Red Pulsed Laser Irradiation on the Mouse Brain

The effect of laser irradiation on mouse dura mater was evaluated prior to perform laser printing experiments. Critical size bone defects were realized on calvaria of six OF-1 male mice, then animals were positioned inside the printing station and laser was directly focused onto dura mater in one site. As laser beam was directly focused on dura mater, the hypothetical deleterious effects on dura mater should be worse than those observed during n-HA printing. Indeed, for n-HA printing, laser focus point was 1.5 mm above dura mater surface. The controlateral site was kept free of laser as negative control. Skin was sutured at the end of the experiment.

Figure 4A:
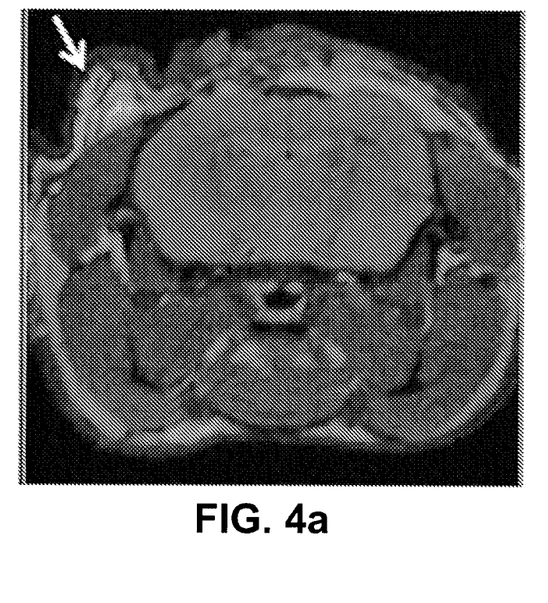
FIGS. 4a and 4b are MRI displays an oedema of dura mater on the test side (arrow) submitted to direct near infra-red pulsed laser irradiation after one week (FIG. 4a) and after 2 weeks (FIG. 4b) in the first experimentation, FIGS. 4a and 4b showing that the oedema has regressed.
Figure 4B:
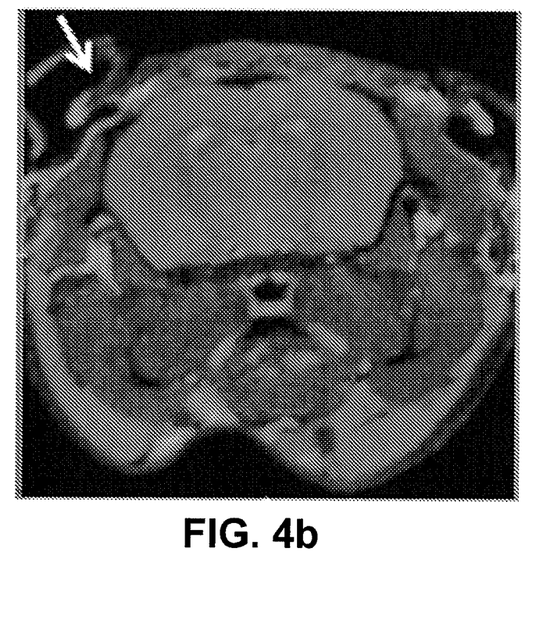

As shown on FIGS. 4a and 4b, inflammation was followed up longitudinally by Magnetic Resonance Imaging (MRI) using a horizontal 4,7 T Biospec system (Bruker, Germany). This system is equipped with a 6 cm gradient insert capable of 950 mT/m maximum strength and 80 µm rise time. Mice were anesthetized with 1.5-2% isofluorane (Centravet, La Palisse, France) mixed in air and then positioned prone within the magnet, with the head placed at the center of the NMR coil. The 3D images were performed with TrueFISP sequence: TE/TR=3.2/6.4 ms, flip angle: 65°, FOV: 30×18×18 mm, matrix: 256×96×96, resolution: 117× 188×188 µm, slice orientation: coronal, reception bandwitdh: 195 Hz/pixel. The total number of averages was equal to 24 (6 per I magnitude images) resulting in a total acquisition time of 23 minutes 26 seconds.

Three animals were sacrificed after one week and the three remaining were sacrificed after one month via exposure to hyperbaric carbon dioxide. The skull and brain were harvested in blocks, and prepared for demineralized histological sections: The samples were demineralized 12 hours (Decalcifiant osseux BAYER, ref 70033, France), then dehydrated in ethanol (70%, 80%, 95%, 100%) then embedded in paraffin. Ten microns coronal sections were cut and stained with Hematoxylin-Eosin-Saffron (HES) and observed under a photomicroscope (Nikon eclipse 80i, The Netherlands). The sections were observed for the presence of inflammation at brain/skull interface.

In Vivo Printing in Mouse Calvaria Defect

Figure 3:
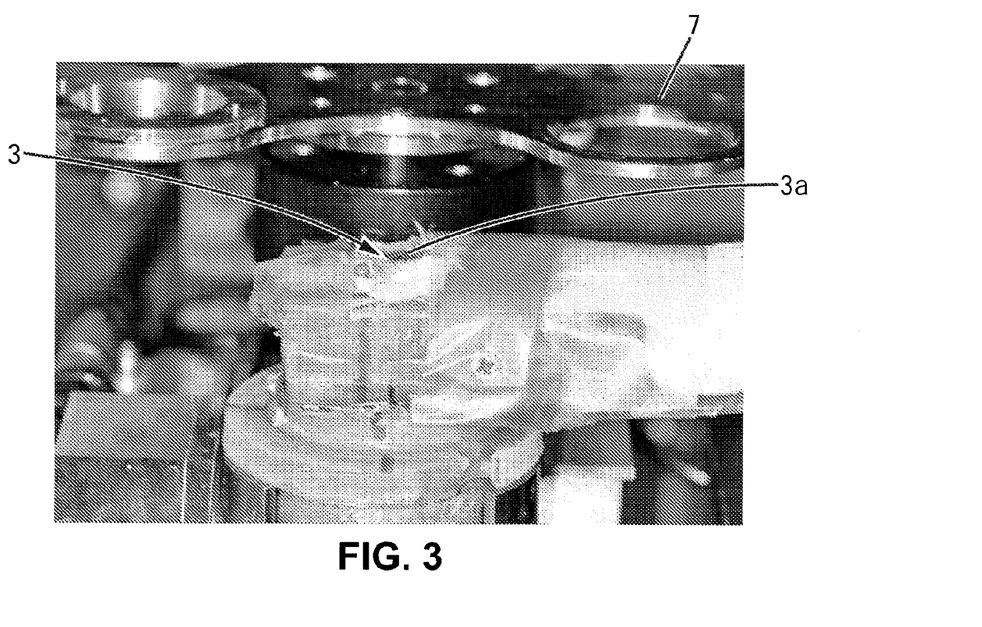
FIG. 3 is a partial lateral view of the Bioprinting station of FIG. 1, illustrating the positioning of the mouse calvaria defects in the first experimentation with respect to a dispenser of biological material.

For in vivo experiments, as shown on FIG. 3, the mouse was installed in the holding device configured to receive the mouse and the calvaria defects were positioned to face the ribbon.

Consequently, the printing method was performed as follow:
- the mouse was placed into its holder, then introduced inside the station onto (x, y, z) motorized translation stages,
- thanks to the video system (i.e. CCD camera with an instantaneous display), the calvaria defects were visualized and focused by translating mouse holder according to the z axis; indeed, dura mater surface was recorded in the software as the position of the substrate following z-axis; this z position was recorded as the physical position of the substrate into the software; the center of the right defect was then targeted through the touchscreen, inducing the translation of the mouse holder according to (x, y) axes. This position is then recorded as the origin of the printed pattern,
- the pattern (a 3 mm in diameter disk) was computed with the software and coupled with laser parameters (power, frequency), a scanning speed and a printing gap distance. In the framework of this study, in agreement with previous studies on laser printing of n-HA, the laser energy was 12 µJ per pulse (with a 40 µm spot size), the frequency was 5 kHz, the scanner speed was 200 mm/s and the printing gap was 1500 µm,
- 3D printing was performed by reproducing this pattern 30 times; between each pattern, the holder was shifted automatically from a given distance equaled to the distance between 2 patterns printed onto the ribbon; before any additional layer, the mouse holder was lowered of 20 µm, what corresponds to the thickness of one n-HA layer;
- at the end of the process, the holder is lowered at a suitable distance to avoid any contact between the mouse and the ribbon.

Thirty OF1 male mice (12 weeks old) were included within this cohort. After the generation of calvaria bone defects, each animal received the same amount of material, which consisted in 30 stacked layers (20 µm each) of n-HA printed by HT Bio-LP in the left defect (test site). The controlateral (right) defect was left empty for negative control (control site). Skin was then sutured and animal were returned to animal facilities.

MRI was used as a non-invasive methodology to evaluate brain inflammation in vivo longitudinally in two animals of the 3 months group at day 7, day 15 and day 30. Parameters used in this study were similar to those presented above.

Regarding n-HA follow-up and new bone formation, mice were sacrificed after one week (mice number, n=10), one month (n=10) or three months (n=10) via exposure to hyperbaric carbon dioxide and the entire heads were removed "in block" and fixed 3 days in 4% PFA. X-ray microtomography acquisitions were done for all samples, using a General Electric pCT. Tension and intensity used for X rays generation were 80 kV and 60 mA, respectively; 800 views were acquired with an exposure time of 3000 ms. The resolution obtained was 0.015 mm. Image J Software was used to evaluate unreconstructed surface of the bone defect. Statistical analyses were performed using Medcalc® software (Belgium). Comparisons of the three independent groups (unpaired samples: one week, one month and three months) were done with the non parametric Mann-Whitney U-test. Differences were considered significant with $p<0.05$.

Finally, three samples of each group were demineralized for histology. Decalcified sections were prepared as described above, stained with Hematoxylin-Eosin-Saffron (HES) and were observed under a photomicroscope (Nikon eclipse 80i, The Netherlands) for the presence of n-HA and newly formed bone.

Results and Discussion

Rationale for Printing n-HA in Calvaria Critical Size Defects Created in Living Mice This above described animal model was retained in order to evaluate in vivo bioprinting potentiality. In spite of the potentially traumatizing process, most of animals recovered rapidly and displayed no sign of infection or neurologic disorders.

In vivo printing of n-HA was carried out using the HT Bio-LP station of the invention.

Hydroxyapatite was chosen because it is the major non-organic component of bone.

As a preliminary result, over thirty male mice, twenty-nine recovered after the whole process, including surgical sequence and further laser printing experiments. Neither wound infection nor neurological disorders were developed in the animals after surgery and n-HA printing. In addition, after bone defect achievement, dura mater was checked for its integrity, what was confirmed by the presence of pulsating blood vessels.

Effect of Near Infra-Red Laser Irradiation on Mice Brain

While Laser-Assisted Bioprinting has been more largely studied using UV pulsed lasers at 248 nm and 355 nm, a nanosecond pulsed laser emitting at 1064 nm was used due to the hypothesized innocuousness of near infrared laser pulses on biological tissues.

Direct laser irradiation was performed on dura mater of six mice, using a similar exposure than for printing experiments.

Figure 5:
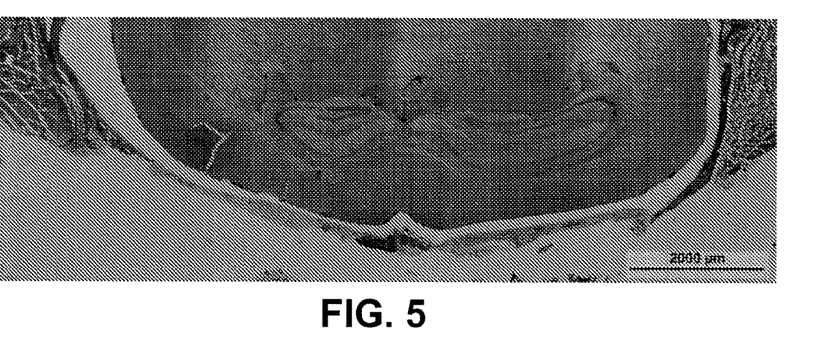
FIG. 5 illustrates a decalcified coronal section of the brain of the mouse in the first experimentation, fifteen days after the calvaria defects were performed and one of them subject to laser irradiation, FIG. 5 showing that the inflammation has regressed and no necrosis is observable on brain tissues.

As shown on FIGS. 4a and 4b, MRI analysis revealed that laser effect and surgical trauma consisted in an oedema beneath the dura mater on test side at day 7, which regressed at day 15 and disappeared after 21 days. Decalcified sections displayed myofibroblasts within both test and control defects, without inflammation or necrosis of nervous and bony tissues (FIG. 5). Based on these experiments, it was concluded that the infra red laser used in this experiment had no deleterious effects on the brain tissues studied.

In Vivo n-HA Printing Inside Calvaria Defects and Bone Repair

Regarding printing of n-HA inside calvaria defects, macroscopic examination at the end of the experiment confirmed the presence of printed material according to the shape of the computer-drawn pattern. Moreover, chemical and biological properties of the printed material were not modified by laser printing.

The follow up of brain inflammation performed by MRI in animals with n-HA printing displayed the same inflammation intensity than previous samples irradiated by laser (see above). Consequently, laser printing of n-HA per se, does not provoke harmful effects on mice brain.

Longitudinal analysis of bone repair was done at three time points (10 mice after one week, 10 mice after one month and 10 mice after three months) based on decalcified histological sections and Micro-computed Tomography.

Figure 6A:
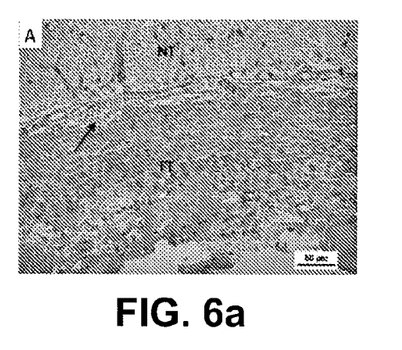
FIGS. 6a, 6b, 6c, 6d, 6e, and 6f are decalcified histology images of the mouse calvaria defects in the first experimentation, the letter B designating Bone; the letters NT designating Nervous Tissues and the letters FT designating Fibrous Tissues on FIG. 6a-6f, FIG. 6a showing laser printed n-HA (arrow) in close contact from brain surface, on the test site, one week after treatment, FIG. 6b showing some n-HA (arrow) at distance from brain surface, at the control site, one week after treatment, FIG. 6c showing mature and immature bone, at test site, one month after treatment, FIG. 6d showing fibrous tissues in the defect, at control site, one month after treatment, FIG. 6e showing mature bone tissue repairing the entire defect at test site, three months after treatment, FIG. 6f showing no bone tissue in the center of the defect, at control site, three months after treatment.
Figure 6B:
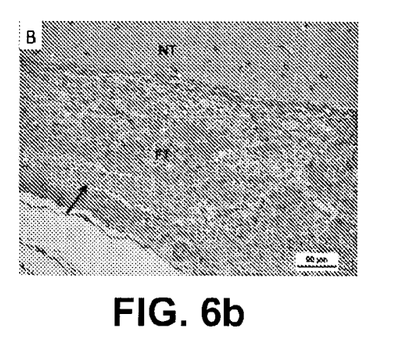
Figure 6C:
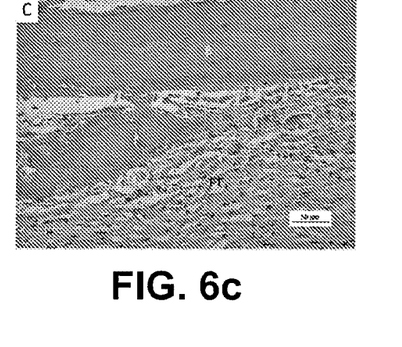
Figure 6D:
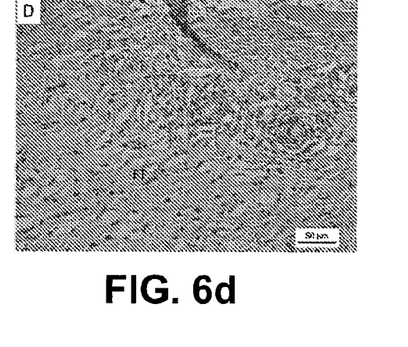
Figure 6E:
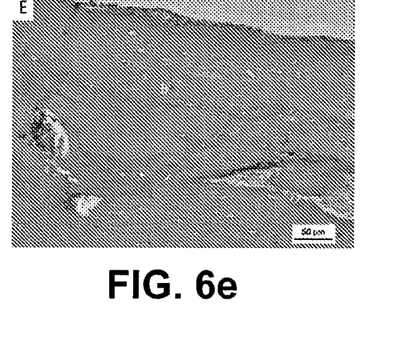
Figure 6F:
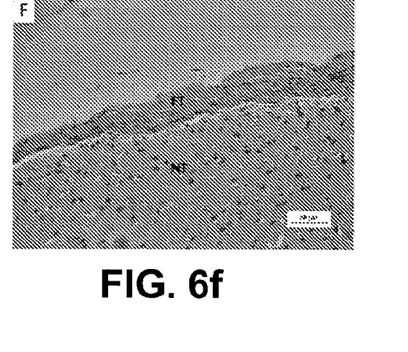
Figure 7:
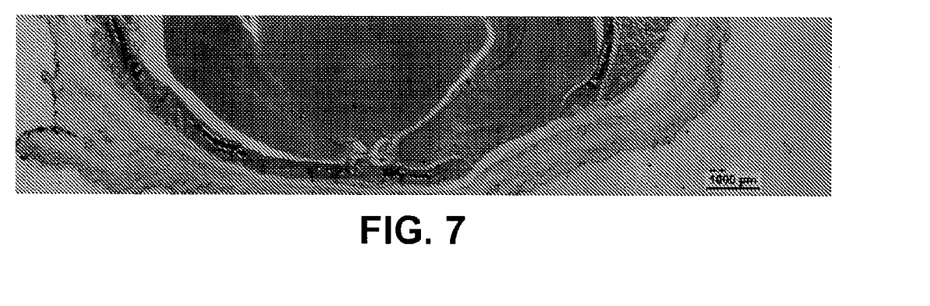
FIG. 7 is a view of decalcified histology of the mouse calvaria defects in the first experimentation, showing a complete bone repair on test side after 3 months (star), the mouse calvaria defect being not reconstructed at the control site (arrow)
Figure 8A:
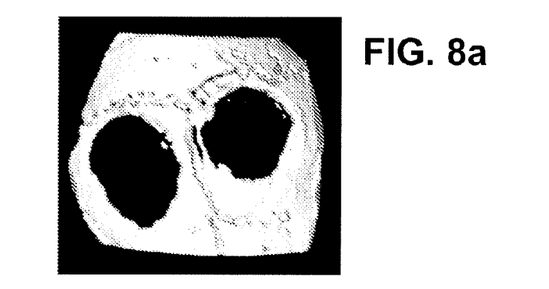
FIGS. 8a and 8b are of X-ray micro-tomography images of the mouse calvaria defects in the first experimentation, one week (FIG. 8a) and one month (FIG. 8b) after treatement.
Figure 8B:
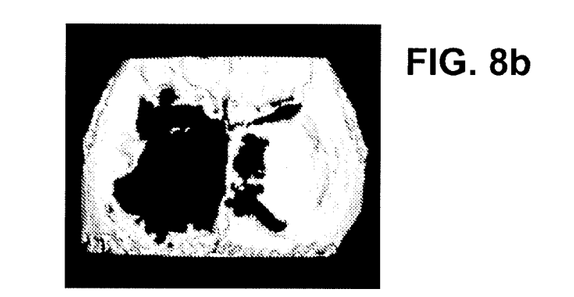

Decalcified sections revealed that the material was present in close contact with dura mater on the test sites after one week (FIG. 6a). After one month, newly formed mature and immature bone and n-HA aggregates inside macrophages were observed in test sites (FIG. 6c), while no bone repair was seen in control sites (FIG. 6d). Three months after printing, mature bone tissue was observed in test sites (FIG. 6e); in control sites (FIG. 6f) bone repair remained incomplete in many cases. In addition, from one week to three months, the amount of n-HA particles observed in situ decreased, probably because of integration of the material in bone remodeling or due to dissolution in the interstitial fluids and phagocytosis by inflammatory cells.

These results were confirmed through X-ray micro-tomography analyses. As can be seen on FIGS. 8a and 8b, bone formation has clearly been observed one month after printing. The unreconstructed surfaces were significantly lower at one month versus one week ($p<0.05$), significantly lower at three months versus one month ($p<0.01$) and significantly lower at three months versus one week ($p<0.01$). Besides, no bone formation occurred in negative control sites at any time.

In some cases, n-Ha material was also observed in the controlateral defect, an area not being concerned by the printing experiment. As shown in FIG. 6b, n-HA can be observed at a distance from the brain surface (control sites, calvaria midline). These n-HA particles may have moved from the printed site due to the absence of immobilization of printed materials into the recipient site. Pressures applied on the skin during suturing and after animal recovery could have thus induced migration of printed n-Ha from the printed defect to the contro-lateral site. In the future, a specific attention will be paid on immobilizing the printed materials and in suturing mouse skin. In this aim, using surgical glue or other biomembranes are envisaged.

Conclusions and Perspectives

In vivo Bioprinting of nano-hydroxyapatite has been performed by means of a CAD-CAM station dedicated to high-throughput Laser-Assisted Bioprinting. These results demonstrate that in vivo printing is possible, and may prove to be helpful in the future for medical robotics and computer-assisted medical interventions.

Upgrading medical robots with Bioprinting ability may allow, first, to improve surgical precision. Indeed, while µL volumes of materials or drugs can be currently handled in the body by surgeons (or actual robots) by using syringes, highly smaller volumes could be deposited using biological printers since these laters can generate droplets of pL volume. Moreover, parallel to volume reduction, spatial resolution will be also largely improved by the use of laser printers or other bioprinters.

Finally, whether in vivo bioprinting appears as an original application of laser technologies, combination of laser printing with other laser-assisted processes (e.g. laser tissue ablation, laser heating, . . . ) could offer new perspectives to robot manufacturers and hence, clinicians.

Second Experimentation

Figure 9:
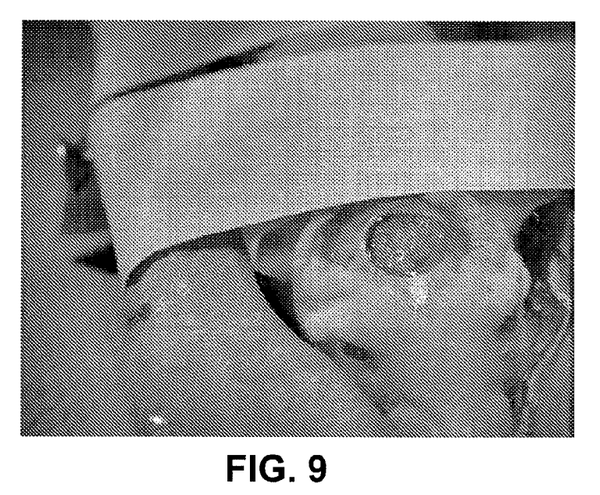
FIG. 9 is a view of a calvaria defect performed on a mouse in a second experimentation implementing the biological printing station of FIG. 1, the second experimentation consisting in an in vivo printing of MG63 cells transfected by Luciferase enzyme (MG63-Luc) as biological material within a midline mouse calvaria defect.
Figure 10:
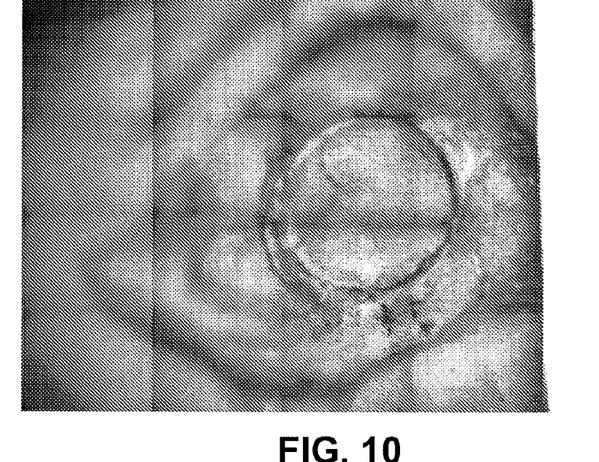
FIG. 10 is a representation of an image of the mouse calvaria defect taken by a camera of an imaging system of the biological printing station of FIG. 1.
Figure 11:
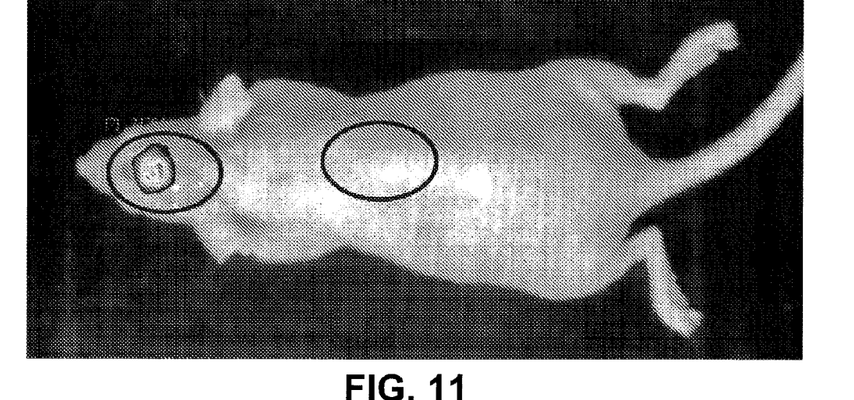
FIG. 11 is representation of an image of the mouse taken by a photon imager of the imaging system of the biological printing station of FIG. 1 after a suitable marker (Luciferin) has been injected.

The second experimentation described in relation to FIGS. 9 to 11, consists in an in vivo printing of MG63 cells transfected by Luciferase enzyme (MG63-Luc) as biological material within a midline mouse calvaria defect.

Materials and Methods

Synthesis of Printable MG63-Luc

In this experimentation, the deposited biological material was a solution of MG63 cells transfected by Luciferase enzyme (MG63-Luc). Cell concentration was 50 Millions cells/ml and cells were suspended in culture medium supplemented with 0.5% Alginate (v/v).

Establishment of Calvaria Critical Size Defect in Mice

In this case, nude mice (Charles River, France) were used to perform a midline calvaria defect of 4 mm wide with diameter trephine burr (TBR Toulouse, France) (see FIG. 9). The preparation of the animal is similar to the above-mentioned procedure.

In Vivo Printing in Mouse Calvaria Defect

The above described biological printing station 1 was used and a ribbon, similar to that described in relation to the first experimentation except for the layer of biological material coating the support, was prepared.

The mouse as a receiving substrate 3 was placed in the positioning system (FIG. 9) with the midline calvaria defect as area of interest facing the opened working area of the holding device and the CCD camera.

The defect was detected by the CCD camera of the imaging system of the biological printing station as can be seen from FIG. 10 showing a video capture of the defect.

According to the defect morphology, a 3 mm-diameter ring pattern was determined. The center of the ring was adjusted to the center of the defect.

Results and Discussion

Macroscopic observation performed immediately after bioprinting exhibit the circle of MG63 cells.

Besides, Luciferin was injected intraperitoneaoulsy for Photon imaging (Biospace, France) analysis. Results of immediate photon imager observations are shown in FIG. 11 that evidenced the presence of a ring-shape pattern of MG63 cells at the position determined preliminary by the imaging system.

This experiment demonstrates that cell printing in vivo is feasible.

Third Experimentation

Figure 12:
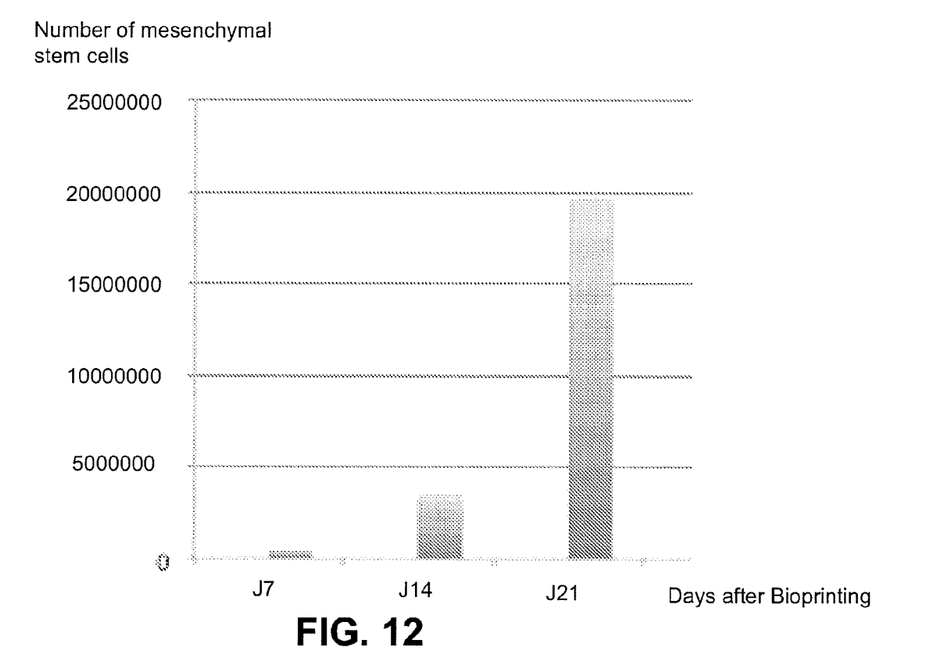
FIG. 12 is a diagram showing the evolution of the number of photons per second per steradian as a function of time after bioprinting in a third experimentation implementing the biological printing station of FIG. 1, the third experimentation consisting in an in vivo printing of murine mesenchymal stem cells (D1 cell line bought from ATCC) transfected by luciferase enzyme as biological material (D1-Luc) within a lateral mouse calvaria defect, the diagram illustrating the proliferation of mesenchymal stem cells.

The third experimentation described in relation to FIG. 12, consists in an in vivo printing of murine mesenchymal stem cells (D1 cell line bought from ATCC) transfected by luciferase enzyme as biological material (D1-Luc) within a lateral mouse calvaria defect.

Materials and Methods

Preparation of a Printable D1-Luc Solution

In this experimentation, the deposited biological material was a solution of D1 cells transfected by Luciferase enzyme (D1-Luc). Cell concentration was 50 Millions cells/ml and cells were suspended in culture medium supplemented with 1% Alginate (v/v).

Establishment of Calvaria Critical Size Defect in Mice

In this case, Balb/c (Charles River, France) were used to perform two lateral calvaria defects of 3.3 mm wide with diameter trephine burr (TBR Toulouse, France). The preparation of the animal is similar to the above-mentioned procedure.

In Vivo Printing in Mouse Calvaria Defect

The above described biological printing station 1 was used and a ribbon, similar to that described in relation to the second experimentation except for the layer of biological material coating the support, was prepared.

The mouse as a receiving substrate 3 was placed in the positioning system with one of the lateral calvaria defects as area of interest facing the opened working area of the holding device and the CCD camera.

The defect was detected by the CCD camera of the imaging system of the biological printing station.

According to the defect morphology, a ring pattern was determined as follow: outer diameter: 3.2 mm and inner diameter: 2.8 mm. The center of the ring was adjusted to the center of the defect.

Results and Discussion

In vivo cell proliferation was followed up to 3 weeks after bioprinting using Photon imaging (Biospace, France). As shown on FIG. 12, mesenchymal stem cells proliferate up to 21 days after bioprinting.

The invention claimed is:

1. Bioprinting method comprising the following steps:
   A—providing a Bioprinting device adapted to deposit a pattern of biological material,
   B—providing a substrate presenting at least one area of interest and a remaining part, said area of interest having a feature that distinguishes said area of interest from the remaining part,
   C—positioning the area of interest with respect to the Bioprinting device,
   D—acquiring an image of the substrate and revealing on the acquired image the feature of the area of interest with respect to the remaining part,
   E—processing the acquired image of the substrate so as to detect the revealed area of interest on the acquired image and to determine the pattern corresponding to the area of interest detected on the acquired image,
   F—depositing onto the area of interest the biological material according to the pattern determined at step E and corresponding to the area of interest detected on the acquired image.

2. Bioprinting method according to claim 1, wherein the step E comprises automatically detecting the revealed area of interest on the acquired image and automatically determining the pattern corresponding to the area of interest detected on the acquired image.

3. Bioprinting method according to claim 1, wherein the area of interest of the substrate has a relief with respect to the remaining part of the substrate as feature, said relief having a geometry, and the step D comprises revealing on the acquired image the relief, the step E comprises detecting the revealed relief on the acquired image and determining the pattern corresponding to the geometry of the relief detected on the acquired image, and the step F comprises forming a biological tissue structure corresponding to the relief.

4. Bioprinting method according to claim 1, wherein the step E further comprises determining a location of the area of interest, and the step F comprises depositing the biological material at the determined location.

5. Bioprinting method according to claim 1, wherein the providing step A includes providing a bioprinting station comprising the bioprinting device and an imaging system, the bioprinting device comprising:
   at least one biological material dispenser comprising a holding device provided with at least one opened working space, and a laser system comprising a laser device for emitting a laser beam adapted to transfer the biological material and an optical scanning device adapted to orient the laser beam within the opened working space, and
   a positioning system,
      wherein step C includes holding at least one ribbon containing the biological material in the holding device of the dispenser with at least a part of the ribbon being received in the opened working space, placing the substrate in the positioning system and positioning the area of interest with respect to the dispenser by the positioning system,
      wherein step D includes driving the imaging system according to an optical pathway to acquire the image of the substrate, the substrate being scanned by moving the optical pathway along the substrate through the optical scanning device of the laser device, and
      wherein step F includes driving the holding device and the positioning system relative to one another so that the opened working space faces the area of interest, and depositing the biological material according to the pattern determined at step E within the opened working space by driving the laser system and the positioning system relative to one another.

* * * * *